US008119137B2

(12) United States Patent
Nieswandt et al.

(10) Patent No.: US 8,119,137 B2
(45) Date of Patent: Feb. 21, 2012

(54) PREVENTION OF THROMBUS FORMATION AND/OR STABILIZATION WITH INHIBITORS OF FACTOR XII OR ACTIVATED FACTOR XII

(75) Inventors: Bernhard Nieswandt, Würzburg (DE); Thomas Renné, Würzburg (DE)

(73) Assignee: CSL Behring GmbH (DE)

( * ) Notice: Subject to any disclaimer, the term of this patent is extended or adjusted under 35 U.S.C. 154(b) by 326 days.

(21) Appl. No.: 11/793,820

(22) PCT Filed: Dec. 20, 2005

(86) PCT No.: PCT/EP2005/013714
§ 371 (c)(1),
(2), (4) Date: Nov. 26, 2007

(87) PCT Pub. No.: WO2006/066878
PCT Pub. Date: Jun. 29, 2006

(65) Prior Publication Data
US 2008/0254039 A1   Oct. 16, 2008

(30) Foreign Application Priority Data
Dec. 23, 2004   (EP) .................................... 04030593

(51) Int. Cl.
*A61K 39/395*   (2006.01)
(52) U.S. Cl. ............... 424/145.1; 424/133.1; 424/141.1; 424/146.1; 514/13.8; 514/14.9; 514/15.3
(58) Field of Classification Search .................. None
See application file for complete search history.

(56) References Cited

U.S. PATENT DOCUMENTS

| | | | |
|---|---|---|---|
| 4,963,657 A * | 10/1990 | Pixley ..................... | 530/388.25 |
| 5,585,259 A | 12/1996 | Lauwereys et al. | |
| 6,613,890 B2 | 9/2003 | White et al. | |
| 2001/0031757 A1 | 10/2001 | Shafer et al. | |
| 2002/0042144 A1 | 4/2002 | Mann et al. | |
| 2003/0109680 A1 | 6/2003 | Wong et al. | |
| 2004/0053206 A1* | 3/2004 | Cicardi et al. ................ | 435/1.1 |
| 2004/0229778 A1 | 11/2004 | Elmaleh et al. | |
| 2005/0075597 A1 | 4/2005 | Vournakis et al. | |
| 2005/0164928 A1* | 7/2005 | Ladner et al. .................. | 514/12 |
| 2006/0034847 A1 | 2/2006 | Yun et al. | |
| 2006/0104944 A1 | 5/2006 | Mousa | |

FOREIGN PATENT DOCUMENTS

| | | |
|---|---|---|
| DE | 19725014 A1 * | 12/1998 |
| EP | 1 669 074 A1 | 6/2006 |
| EP | 1 222 929 B1 | 5/2010 |
| EP | 1 669 074 B1 | 6/2010 |
| WO | WO 95/07986 | 3/1995 |
| WO | WO 03103475 A2 * | 12/2003 |
| WO | WO 2004/004640 A2 | 1/2004 |
| WO | WO 2004/004640 A3 | 1/2004 |
| WO | WO 2004/100982 A1 | 11/2004 |
| WO | WO 2004/110356 A2 | 12/2004 |
| WO | WO 2004/110356 A3 | 12/2004 |
| WO | WO 2005/112989 A1 | 12/2005 |
| WO | WO 2006/021744 A1 | 3/2006 |

OTHER PUBLICATIONS

Laub et al., Chest. Nov. 1994;106(5):1370-5.*
English language abstract of DE19725014A1, published Jun. 13, 1997, entered by DERVENT as 1999-046858.*
Ambrosetti et al. (Chest 2004 125:191-196).*
Agostini, et al., "Inactivation of Factor XII Active Fragment in Normal Plasma, Predominant Role of C1-inhibitor", XP-002368185, Journal of Clinical Investigation, vol. 73, No. 6, pp. 1542-1549, (1984).
Colman, "Overview of Hemostasis", Hemostasis and Thrombosis, Basic Priciples and clinical practice, Lippincott Co., Philadelphia, PA, p. 9, col. 1, paragraph 3 to col. 2, paragraph 1, (1987).
Nuijens, et al., "Activation of the Contact System of Coagulation by a Monoclonal Antibody Directed Against a Neodeterminant in the Heavy Chain Region of Human Coagulation Factor XII (Hageman Factor)", The Journal of Biological Chemistry, XP 000045720, vol. 264, No. 22, pp. 12941-12949, (1989).
Pixley, et al., "The Contact System Contributes to Hypotension but Not Disseminated Intravascular Coagulation in Lethal Bacteremia, In Vivo Use of a Monoclonal Anti-Factor XII Antibody to Block Contact Activation in Baboons", Contact System and Hypotensive Bacteremia, XP-002339809, J. Clin. Invest., vol. 91, No. 1, pp. 61-68, (Jan. 1993).
Rayon, et al., "Monoclonal Antibody F1 Binds to the Kringle Domain of Factor XII and Induces Enhanced Susceptibility for Cleavage by Kallikrein", XP-002368184, Blood, vol. 86, No. 11, pp. 4134-4143, (Dec. 1, 1995).
Schneider, et al., "Differential Effects of Anticoagulants on the Activation of Platelets Ex Vivo", Circulation, vol. 96, No. 9, XP002921927, pp. 2877-2883, (Nov. 4, 1997).
Feuerstein, et al., "Antithrombotic Efficacy of a Novel Murine Anti-human Factor IX Antibody in Rats", XP002938580, Arterioscler. Thromb. Vasc. Biol., vol. 19, No. 10, pp. 2554-2562, (1999).
Refino, et al., "A Human Antibody that Binds to the γ-carboxyglutamic Acid Domain of Factor IX is a Potent Antithrombotic In Vivo", XP-000857692, Thrombosis and Haemostasis, vol. 82, No. 3, pp. 1188-1195, (1999).
Chu, et al., "Anticoagulant Potential of an Antibody Against Factor VII", Journal of Surgical Research, XP-002340056, vol. 114, pp. 37-41, (2003).
Jacquemin, et al., "The Use of Antibodies to Coagulation Factors for Anticoagulant Therapy", XP008050898, Current Medicinal Chemistry, pp. 2291-2296, (2004).
Renné, et al., "Defective thrombus formation in mice lacking coagulation factor XII", JEM, XP-002339811, vol. 202, No. 2, pp. 271-281, (Jul. 18, 2005).

(Continued)

*Primary Examiner* — Michael Szperka
(74) *Attorney, Agent, or Firm* — Finnegan, Henderson Farabow, Garrett & Dunner, LLP

(57) ABSTRACT

The present invention relates to the use of at least one antibody and/or one inhibitor for inhibiting factor XII and preventing the formation and/or the stabilization of three-dimensional thrombi. It also relates to a pharmaceutical formulation and the use of factor XII as an anti-thrombotic target.

12 Claims, 7 Drawing Sheets

OTHER PUBLICATIONS

Figure 1:
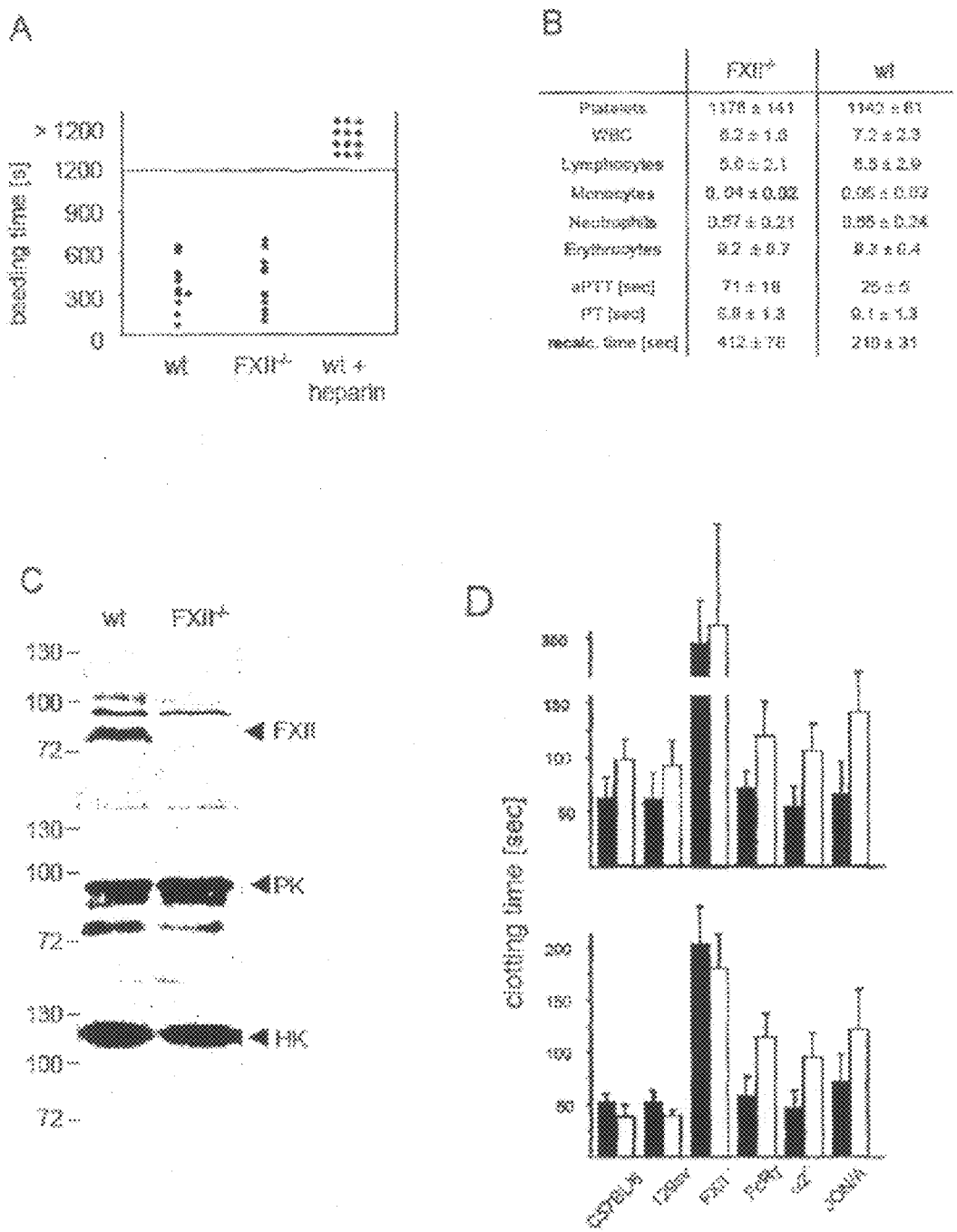

Colman, R.W., "Are hemostasis and thrombosis two sides of the same coin?", J. Exp. Med. 203:493-495 (2006).
EPO Communication pursuant to Article 94(3) EPC (Nov. 26, 2009), 5 pages.
Capasso, G., et al., Preliminary results with peritendinous protease inhibitor injections in the management of Achilles tendinitis, *J. Sports Traumatol. rel. res.*, 15(1): 37-43 (1993).
Stassen, Jean Marie, et al., Characterisation of a Novel Series of Aprotinin-derived Anticoagulants, *Thrombosis and Haemostasis*, 74(2): 655-59 (1995).
Williams, A. and Baird, L. G., DX-88 and HAE: a developmental perspective, *Transfusion and Apheresis Science*, 29: 255-58 (2003).
Aronson, D.L., et al., Platelet-Dependent Thrombin Generation After In Vitro Fibrinolytic Treatment, *Circulation*, 85(5):1706-12 (1992).
Chen, Zhi-Yuan, et al., Inhibition of Plant-Pathogenic Fungi by a Corn Trypsin Inhibitor Overexpressed in *Escherichia coli*, *Applied and Environmental Microbiology*, 65(3) 1320-24 (Mar. 1999).
Colman, R. W., et al., eds. Hemostasis and Thrombosis, *Basic Principles & Clinical Practice*, 69, 103-121, 321-22, 4th Edition (2001).
Gailani, D., et al., A murine model of factor XI deficiency, *Blood Coagulation and Fibrinolysis*, 8: 134-44 (1997).
Girolami, A., et al., The Occasional Venous Thromboses Seen in Patients with Severe (Homozygous) FXII Deficiency are Probably Due to Associated Risk Factors: A Study of Prevalence in 21 Patients and Review of the Literature, *J. Thrombosis and Thrombolysis*, 17(2): 139-143 (2004).
Grüner, S., et al., Multiple integrin-ligand interactions synergize in shear-resistant platelet adhesion at sites of arterial injury in vivo, *Blood*, 102: 4021-27 (2003).
Haaseman, M., et al., Anti-idiotypic antibodies bearing the internal image of a bradykinin epitope. Production, characterization, and interaction with the kinin receptor, *J. Immunology*, 147: 3882-92 (1991).
Halbmayer, W.M., et al., Factor XII (Hageman Factor) Deficiency: A Risk Factor in the Development of Thromboembolism. Incidence of Factor XII Deficiency in Outpatients Suffering from Recurrent Venous or Arterial Thromboembolism and Myocardial Infarction, *Wien. Med. Wochenschr*, 143(2): 43-50 (1993).
Isawa, Haruhiko, et al., A Mosquito Salivary Protein Inhibits Activation of the Plasma Contact System by Binding to Factor XII and High Molecular Weight Kininogen, *J. Biological Chemistry*, 277(31): 27651-58 (2002).
Holtkötter, O., et al. Integrin $\alpha_2$-Deficient Mice Develop Normally, Are Fertile, but Display Partially Defective Platelet Interaction with Collagen, *J. Biological Chemistry*, 277(13): 10789-94 (2002).
Jin L., et al., Crystal Structures of the FXIa Catalytic Domain in Complex with Ecotin Mutants Reveal Substrate-Like Interactions, *J. Biological Chemistry*, 280(6): 4704-12 (2005).
Koster, T., et al., John Hageman's factor and deep-vein thrombosis: Leiden Thrombophilia Study, *British Journal of Haematology*, 87: 422-24 (1994).
Kuhli, C., et al., Factor XII Deficiency: a Thrombophilic Risk Factor for Retinal Vein Occlusion, *Am. J. Ophthalmology*, 137(3): 459-464 (2004).
Laemmli, U.K., Cleavage of Structural Proteins during the Assembly of the Head Bacteriophage T4, *Nature*, 227: 680-85 (1970).
Mackman, N., Role of Tissue Factor in Hemostasis, Thrombosis, and Vascular Development, *Arterioscler. Thromb. Vasc. Biol.*, 24: 1015-22 (2004).
Massberg, S., et al., Increased Adhesion and Aggregation of Platelets Lacking Cyclic Guanosine 3',5'-Monophosphate Kinase I, *J. Exp. Med.*, 189(8): 1255-63 (1999).
Massberg, S., et al., A Crucial Role of Glycoprotein VI for Platelet Recruitment to the Injured Arterial Wall In Vivo, *J. Exp. Med.*, 197(1): 41-49 (2003).
Nieswandt, B., et al., Flow-Cytometric Analysis of Mouse Platelet Function, *Methods Mol. Biol.* 272: 255-68 (2004).
Pauer, H.U., et al., Targeted deletion of murine coagulation factor XII gene—a model for contact phase activation in vivo, *Thromb. Haemost.*, 92: 503-08 (2004).
Ratnoff, O.D. & Colopy, J.E., A Familial Hemorrhagic Trait Associated with a Deficiency of a Clot-Promoting Fraction of Plasma, *J. Clin. Invest.*, 34(4): 602-13 (1955).
Ravon, D., et al., Monoclonal Antibody F1 Binds to the Kringle Domain of Factor XII and Induces Enhanced Susceptibility for Cleavage by Kallikrein, *Blood*, 86(11):4134-43 (1995).
Takai, T., et al., FcR γ Chain Deletion Results in Pleiotrophic Effector Cell Defects, *Cell*, 76: 519-29 (1994).
Wang, X., et al., Effects of factor IX or factor XI deficiency on ferric chloride-induced carotid artery occlusion in mice, *J. Thromb. Haemostasis*, 3: 695-702 (2005).
Williams, A. & Baird, L.G., DX-88 and HAE: a developmental perspective, *Transfusion and Apheresis Science*, 29: 255-58 (2003).
Zeerleder, S., et al., Reevaluation of the Incidence of Thromboembolic Complications in Congenital Factor XII Deficiency. A Study on 73 Subjects from 14 Swiss Families, *Thromb. Haemost*, 82: 1240-46 (1999).
Siemens, *BCS XP System*, Overview, Features & Benefits, Assay Menu ("Endogenous Thrombin Potential (ETP) Assay").
Official Action dated Sep. 6, 2010, in Chinese Application No. 200580046575.6 (6 pages).
Ratnoff, O.D., "Studies on the Inhibition of Ellagic Acid-Activated Hageman Factor (Factor XII) and Hageman Factor Fragments," *Blood*, vol. 57(1): 55-58 (1981).
Makarov, V.A. and Kondratyeva, T.B., "Application of Heparins in Clinical Practice," *Russian Medical Journal*, vol. 6(3) (1998) (4 pages).
Wen, L., et al., "Nucleotide sequence of a cDNA clone that encodes the maize inhibitor of trypsin and activated Hageman factor," *Plant Mol. Biol.* 18: 813-14 (1992).
English translation of Russian Official Action in Russian Application No. 2007123797/14 (025925) (4 pages).
Bolli, R., et al., "Role of Cellular Proteinases in Acute Myocardial Infarction I. Proteolysis in Nonischemic and Ischemic Rat Myocardium and the Effects of Antipain, Leupeptin, Pepstatin and Chymostatin Administered in Vivo," *JACC*, 2(4): 671-80 (1983).
Bolli, R., et al., "Role of Cellular Proteinases in Acute Myocardial Infaction II. Influence of in Vivo Suppression of Myocardial Proteolysis by Antipain, Leupeptin and Pepstatin on Myocardial Infarct Size in the Rat," *JACC*, 2(4): 681-88 (1983).
Office Action of Japanese Patent Application No. 2007-547323, mailed Aug. 2, 2011 (5 pages).
Sase, T. and Wada, H., "Practical disease-tailored antithrombotic therapies," *Rinshōi*, 28(11): 2319-21 (2002).
Ulmer, J. S., et al., "Ecotin is a potent inhibitor of the contact system proteases factor XIIa and plasma kallikrein," *FEBS Letters*, 365: 159-163 (1995).
Wang, K. and Yuen, P., "Calpain inhibition: an overview of its therapeutic potential," *TiPS*, 15(11): 412-419 (1994).
Yamamoto, H., "Experimental Observation of Aprotinin on Platelet Aggregation Induced by Various Kinds of Inducers," *J. of Tokyo Medical College*, 36(5): 595-601 (1978).

* cited by examiner

Figure 6
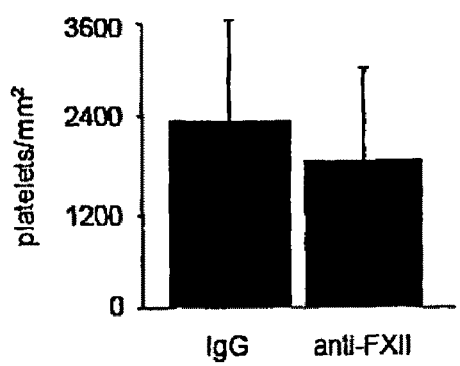
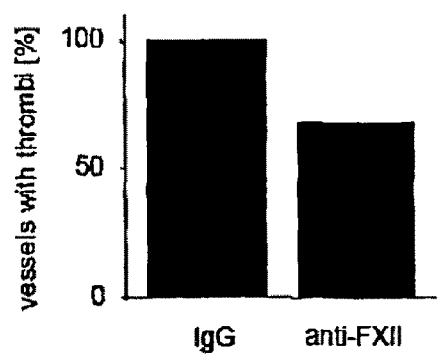
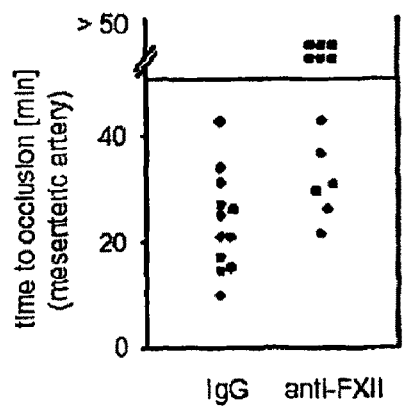

Figure 7
A
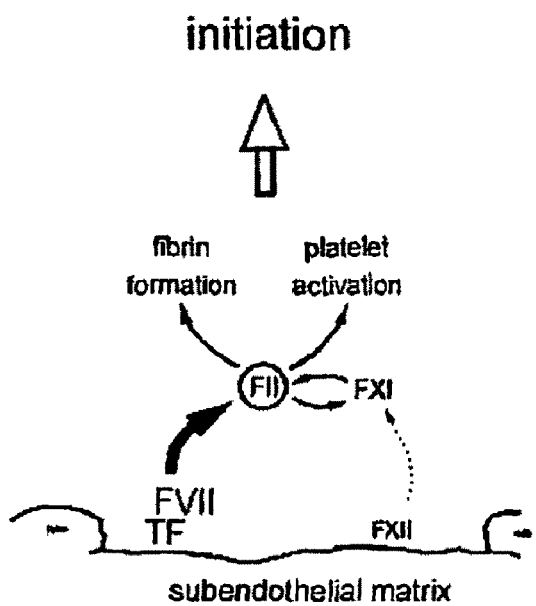
B
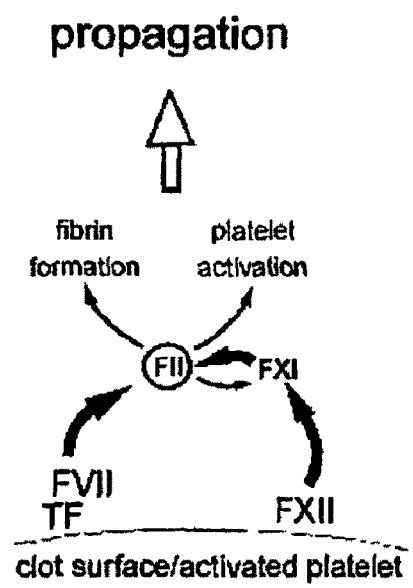

PREVENTION OF THROMBUS FORMATION AND/OR STABILIZATION WITH INHIBITORS OF FACTOR XII OR ACTIVATED FACTOR XII

The subject of the present invention is, in the most general aspect, the prevention of the formation and/or stabilization of three-dimensional arterial or venous thrombi.

In particular the present invention relates to the use of at least one antibody and/or one inhibitor for inhibiting factor XII activity and preventing the formation and/or the stabilization of thrombi and thrombus growth. It also relates to a pharmaceutical formulation and the use of factor XII as an anti-thrombotic target.

Vessel wall injury triggers sudden adhesion and aggregation of blood platelets, followed by the activation of the plasma coagulation system and the formation of fibrin-containing thrombi, which occlude the site of injury. These events are crucial to limit posttraumatic blood loss but may also occlude diseased vessels leading to ischemia and infarction of vital organs. In the waterfall or cascade model, blood coagulation proceeds by a series of reactions involving the activation of zymogens by limited proteolysis culminating in the fulminant generation of thrombin, which converts plasma fibrinogen to fibrin and potently activates platelets. In turn, collagen- or fibrin-adherent platelets facilitate thrombin generation by several orders of magnitude by exposing procoagulant phosphatidyl serine (PS) on their outer surface which propagates assembly and activation of coagulation protease complexes and by direct interaction between platelet receptors and coagulation factors.

Two converging pathways for coagulation exist that are triggered by either extrinsic (vessel wall) or intrinsic (blood-borne) components of the vascular system. The "extrinsic" pathway is initiated by the complex of the plasma factor VII (FVII) with the integral membrane protein tissue factor (TF), an essential coagulation cofactor that is absent on the luminal surface but strongly expressed in subendothelial layers of the vessel. TF expressed in circulating microvesicles might also contribute to thrombus propagation by sustaining thrombin generation on the surface of activated platelets.

The "intrinsic" or contact activation pathway is initiated when factor XII (FXII, Hageman factor) comes into contact to negatively charged surfaces in a reaction involving high molecular weight kininogens and plasma kallikrein. FXII can be activated by macromolecular constituents of the subendothelial matrix such as glycosaminoglycans and collagens, sulfatides, nucleotides and other soluble polyanions or non-physiological material such as glass or polymers. One of the most potent contact activators is kaolin and this reaction serves as the mechanistic basis for the major clinical clotting test, the (activated) partial thromboplastin time (PTT, aPTT). In reactions propagated by platelets, activated FXII then activates FXI and FXIa in turn activates factor IX. Despite its high potency to induce blood clotting in vitro, the (patho) physiological significance of the FXII-triggered intrinsic coagulation pathway is questioned by the fact that hereditary deficiency of FXII as well as of high molecular weight kininogen and plasma kallikrein is not associated with bleeding complications. Together with the observation that humans and mice lacking extrinsic pathway constituents, such as TF, FVII or factor IX, suffer from severe bleeding this has lead to the current hypothesis that fibrin formation is in vivo exclusively initiated by the extrinsic cascade (Mackman, N. (2004). Role of tissue factor in hemostasis, thrombosis, and vascular development. Arterioscler. Thromb. Vasc. Biol. 24, 1015-1022).

Like all physiological mechanisms, the coagulation cascade can become activated inappropriately and result in the formation of haemostatic plugs inside the blood vessels. Thereby, vessels can become blocked and the blood supply to distal organs limited. This process is known as thromboembolism and is associated with high mortality. In addition, the use of prosthetic devices that are in contact with blood is severely limited because of activation of the coagulation cascade and coating of the prosthetic surface, often compromising its function. Examples of such prosthetic devices are haemodialysers, cardiopulmonary by-pass circuits, vascular stents and in-dwelling catheters. In cases where such devices are used, anticoagulants, such as heparin, are used to prevent fibrin from depositing on the surface. However, some patients are intolerant of heparin, which can cause heparin induced thrombocytopenia (HIT) resulting in platelet aggregation and life threatening thrombosis. Furthermore, an intrinsic risk of all anticoagulants used in clinics is an associated increased risk of serious bleeding. Therefore, a need for new types of anticoagulant exists that is not associated with such complications and that can be used in affected patients or as superior therapy concept preventing thrombosis without increased bleeding tendencies.

Hence, it is apparent that there still exists a need for an improved medication for the treatment or prophylaxis of thrombosis and similar disorders. Therefore, it is an object of the present invention to satisfy such a need. For more than five decades it has been known that deficiency of coagulation factor XII is not associated with increased spontaneous or injury related bleeding complications (Ratnoff, O. D. & Colopy, J. E. (1955) A familial hemorrhagic trait associated with a deficiency of a clot-promoting fraction of plasma. J Clin Invest 34, 602-13). Indeed, although presenting a pathological aPTT (a clinical clotting test that addresses the intrinsic pathway of coagulation) humans that are deficient in FXII do not suffer from abnormal bleeding even during major surgical procedures (Colman, R. W. Hemostasis and Thrombosis. Basic principles & clinical practice (eds. Colman R. W., Hirsch. J., Mader V. J., Clowes A. W., & George J.) 103-121 (Lippincott Williams & Wilkins, Philadelphia, 2001). In contrast, deficiency of FXII had been associated with increased risk of venous thrombosis (Kuhli, C., Scharrer, I., Koch, F., Ohrloff, C. & Hattenbach, L. O. (2004) Factor XII deficiency: a thrombophilic risk factor for retinal vein occlusion. Am. J. Opthalmol. 137, 459-464., Halbmayer, W. M., Mannhalter, C., Feichtinger, C., Rubi, K. & Fischer, M. (1993) Factor XII (Hageman factor) deficiency: a risk factor for development of thromboembolism. Incidence of factor XII deficiency in patients after recurrent venous or arterial thromboembolism and myocardial infarction. Wien. Med. Wochenschr. 143, 43-50.). Studies and case reports supporting this idea refer to the index case for FXII deficiency, Mr. John Hageman, who died of pulmonary embolism. The hypothesis that FXII deficiency is associated with an increased prothrombotic risk is challenged by a recent reevaluation of several case reports linking FXII deficiency with thrombosis (Girolami, A., Randi, M. L., Gavasso, S., Lombardi, A. M. & Spiezia, F. (2004) The Occasional Venous Thromboses Seen in Patients with Severe (Homozygous) FXII Deficiency are Probably Due to Associated Risk Factors: A Study of Prevalence in 21 Patients and Review of the Literature. J. Thromb. Thrombolysis 17, 139-143). In most cases the authors identified concomitant congenital or acquired prothrombotic risk factors in combination with factor FXII deficiency that could be responsible for the thrombotic event independently of FXII. The largest epidemiological studies using well characterized patients (Koster, T., Rosendaal, F. R., Briet, E. & Vandenbroucke, J. P. (1994) John Hageman's factor and deep-vein thrombosis: Leiden thrombophilia Study. Br. J. Haematol. 87, 422-424) and FXII-deficient families (Zeerleder, S. et al. (1999) Reevaluation of the incidence of thromboembolic complications in congenital factor XII deficiency—a study on 73 subjects from 14 Swiss families. Thromb. Haemost. 82, 1240-1246) indicated that there is no correlation of FXII deficiency and any pro- or anti-thrombotic risk.

Surprisingly and in contrast to common belief of those skilled in the art the applicant has discovered that the factor XII-driven intrinsic coagulation pathway is essential for arterial thrombus formation in vivo but not necessary for normal tissue-specific hemostasis. Unexpectedly, these results change the long-standing concept that blood clotting in vivo is exclusively mediated by the extrinsic pathway and place factor XII in a central position in the process of pathological thrombus formation.

Accordingly, the first subject of the invention is the use of at least one antibody and/or at least one inhibitor for inhibiting factor XII and preventing the formation and/or the stabilization of three-dimensional arterial or venous thrombi. The anti-FXII antibody respective inhibitor may hereby function so as inhibiting the activation of FXII and/or interfere with other portions of the FXII molecule that are critically involved in FXII activation.

Together with the fact that the intrinsic pathway is not required for hemostasis, this establishes factor XII as a promising new target for powerful antithrombotic therapy. In addition these results are important for the development of anti-FXII agents to control other contact system-linked (patho) mechanisms such as inflammation, complement activation, fibrinolysis, angiogenesis and kinin formation.

Therefore, the present invention further provides the use of such an antibody and/or inhibitor in the treatment or prophylaxis of a condition or disorder related to arterial thrombus formation, i.e. stroke or myocardial infarction, inflammation, complement activation, fibrinolysis, angiogenesis and/or diseases linked to pathological kinin formation such as hypotonic shock, edema including hereditary angioedema, bacterial infections, arthritis, pancreatitis, or articular gout.

In particular, the use of at least one anti-FXII antibody (e.g. like F1 antibody (MoAb F1, Ravon et al., Blood. 1995 Dec. 1; 86(11):4134-43)) and/or the use of at least one protease inhibitor to inhibit FXII-driven thrombus formation is according to the present invention.

Especially preferred is the protease inhibitor selected from for example AT III inhibitor, angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Pro-aldehyde-dimethyl acetate, DX88 (Dyax Inc., 300 Technology Square, Cambridge, Mass. 02139, USA; cited in: Williams A. and Baird LG., Transfus Apheresis Sci. 2003 December: 29 (3):255-8), leupeptin, inhibitors of prolyl oligopeptidase such as Fmoc-Ala-Pyr-CN, corn-trypsin inhibitor, mutants of the bovine pancreatic trypsin inhibitor, ecotin, YAP (yellowfin sole anticoagulant protein) and *Cucurbita maxima* trypsin inhibitor-V including *Cucurbita maxima* isoinhibitors.

Accordingly, the present invention provides the use of such an antibody and/or inhibitor described herein in medicine; and also the use of such an antibody and/or inhibitor in the manufacture of a medicament.

Therefore, according to another aspect of the present invention, a pharmaceutical formulation is provided comprising at least one antibody and/or one inhibitor, which is suitable for inhibiting factor XII and which prevents the formation and/or the stabilization of three-dimensional arterial or venous thrombi.

In particular, the antibody used for the pharmaceutical formulation is an anti-FXII antibody (e.g. like F1 antibody (MoAb F1, Ravon et al., Blood. 1995 Dec. 1; 86(11):4134-43)), and the inhibitor is a protease inhibitor, for example but not limited to AT III inhibitor, angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Pro-aldehyde-dimethyl acetate, DX88 (Dyax Inc., 300 Technology Square, Cambridge, Mass. 02139, USA; cited in: Williams A. and Baird LG., Transfus Apheresis Sci. 2003 December: 29 (3):255-8), leupeptin, inhibitors of prolyl oligopeptidase such as Fmoc-Ala-Pyr-CN, corn-trypsin inhibitor, mutants of the bovine pancreatic trypsin inhibitor, ecotin, YAP (yellowfin sole anticoagulant protein) and *Cucurbita maxima* trypsin inhibitor-V including Curcurbita maxima isoinhibitors.

The antibody may also be a fragment of same or mimetic retaining the inhibitory activity, for example analogues of Kunitz Protease Inhibitor domain of amyloid precursor protein as disclosed in U.S. Pat. No. 6,613,890 especially in columns 4 through 8. Other suitable inhibitors may be Hamadarin as disclosed by Harahiko Isawa et al. in The Journal of Biological Chemistry, Vol. 277, No. 31 (August 2, pp. 27651-27658, 2002). A suitable Corn Trypsin Inhibitor and methods of its production are disclosed in Zhi-Yuan Chen et al., Applied and Environmental Microbiology, March 1999, p. 1320-1324 and reference 19 cited ibidem. All references cited are incorporated for reference including their entire content in this application. Last not least, small molecules isolated for example via use of FXII respective FXIIa inhibition as the assay on which selection is based are part of the invention, as well as their respective use described above or below. These small molecule FXIIa inhibitors could be designed on the bases of a crystal structure of FXII. Therefore several FXII domains or the light chain could be expressed recombinantly in expression systems such as *E. coli*, yeast or mammalian cells. Then the protein is purified and crystallized using standard procedures as described for the FXII substrate FXI (Jin L, et al. (2005) Crystal structures of the FXIa catalytic domain in complex with ecotin mutants reveal substrate-like interactions. J Biol. Chem. 280(6):4704-12.) Alternatively, small molecule serine protease inhibitors could be included to stabilize the FXII structure. Such formulations comprising small molecule inhibitors of protein targets, which can be for example designed guided by crystals of these target proteins, are well known in the art and include pharmaceutical formulations that may be, for example, administered to a patient systemically, such as parenterally, or orally or topically.

The term "parenteral" as used here includes subcutaneous, intravenous, intramuscular, intra-arterial and intra-tracheal injection, instillation, spray application and infusion techniques. Parenteral formulations are preferably administered intravenously, either in bolus form or as a constant infusion, or subcutaneously, according to known procedures. Preferred liquid carriers, which are well known for parenteral use, include sterile water, saline, aqueous dextrose, sugar solutions, ethanol, glycols and oils.

Tablets and capsules for oral administration may contain conventional excipients such as binding agents, fillers, lubricants and wetting agents, etc. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles and preservatives.

Formulations suitable for topical application may be in the form of aqueous or oily suspensions, solutions, emulsions, gels or, preferably, emulsion ointments. Formulations useful for spray application may be in the form of a sprayable liquid or a dry powder.

According to a third aspect of the present invention, the use of factor XII as an anti-thrombotic target by inhibiting factor XII by at least one antibody and/or one inhibitor and preventing therefore the formation and/or the stabilization of three-dimensional thrombi in the vessel is provided.

The nature, benefit, and further features of the present invention become apparent from the following detailed description of the performed experiments and their results when read in conjunction with the accompanying figures described below.

Factor XII-deficient mice were used to analyze the function of the intrinsic coagulation cascade in hemostasis and thrombosis. Intravital fluorescence microscopy and ultrasonic flow measurements revealed a severe defect in the formation and stabilization of three-dimensional thrombi in different arterial branches of the vascular system. Reconstitution of the mutant mice with human factor XII restored the intrinsic coagulation pathway in vitro and arterial thrombus formation in vivo. Mechanistically, the procoagulant activity of the intrinsic pathway was critically promoted by activated platelets. These results place the FXII-induced intrinsic blood coagulation cascade in a central position in the process of arterial thrombus form ation linking plasmatic coagulation with platelet aggregation.

FIG. 1 describes the coagulation analysis of FXII deficient mice: (A) Tail bleeding times of wild-type (n=12) and FXII-/- (n=11) mice. Each symbol represents one individual. (B) Peripheral blood counts in thousands/µl and global coagulation parameters of FXII-/- and wt mice. The abbreviations are white blood counts (WBC), activated partial thromboplastin time (aPTT) and prothrombin time (PT). Values give mean values±SD of 10 mice of each genotype. (C) Contact system proteins FXII, plasma kallikrein (PK) and high molecular weight kininogen (HK) probed in 0.3 µl wt and FXII-/- plasma by Western blotting using specific antibodies. A molecular weight standard is given on the left. (D) Recalcification clotting times were determined in platelet free (upper panel) and platelet rich (lower panel) plasma from C57BL/6 and 129sv wt, FXII-/-, FcRγ-/- and integrin α2-deficient mice following activation with kaolin (dark columns) or collagen (light columns). The effect of JON/A was analyzed in C57BL/6 plasma supplemented with 50 µg/ml antibody. Means±STD from 6 experiments are given.

Figure 2:
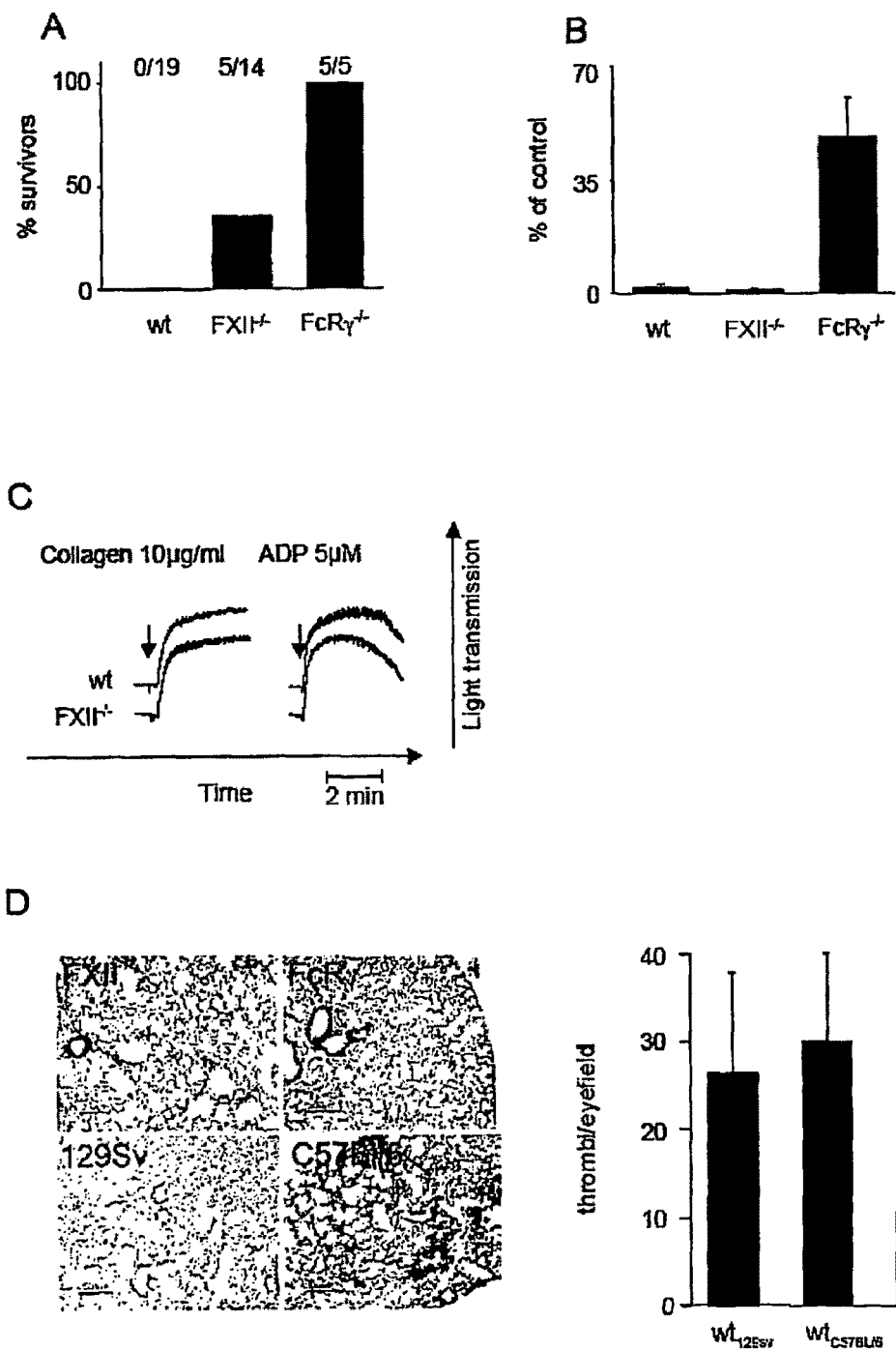

FIG. 2. (A) Thromboembolic mortality was observed following the intravenous injection of collagen (0.8 mg/kg) and epinephrine (60 µg/kg). All wild-type mice died within 5 min. Animals that were alive 30 min after challenge were considered survivors. (B) Platelet counts in control (n=19), FXII-/- (n=14) and FcRγ-/- (n=5) mice 2 min after infusion of collagen/epinephrine. (C) Heparinized platelet rich plasma from wild-type and FXII-/- mice was stimulated with collagen (10 µg/ml) or ADP (5 µM) and light transmission was recorded in a standard aggregometer. The results shown are representative of six mice per group. (D) Hematoxilin/Eosinstained sections from lungs of the indicated mice 2 min after collagen/epinephrine injection. Thrombi per eyefield ware counted in 20× magnification. The bars represent means±SDT from 100 eyefields.

Figure 3:
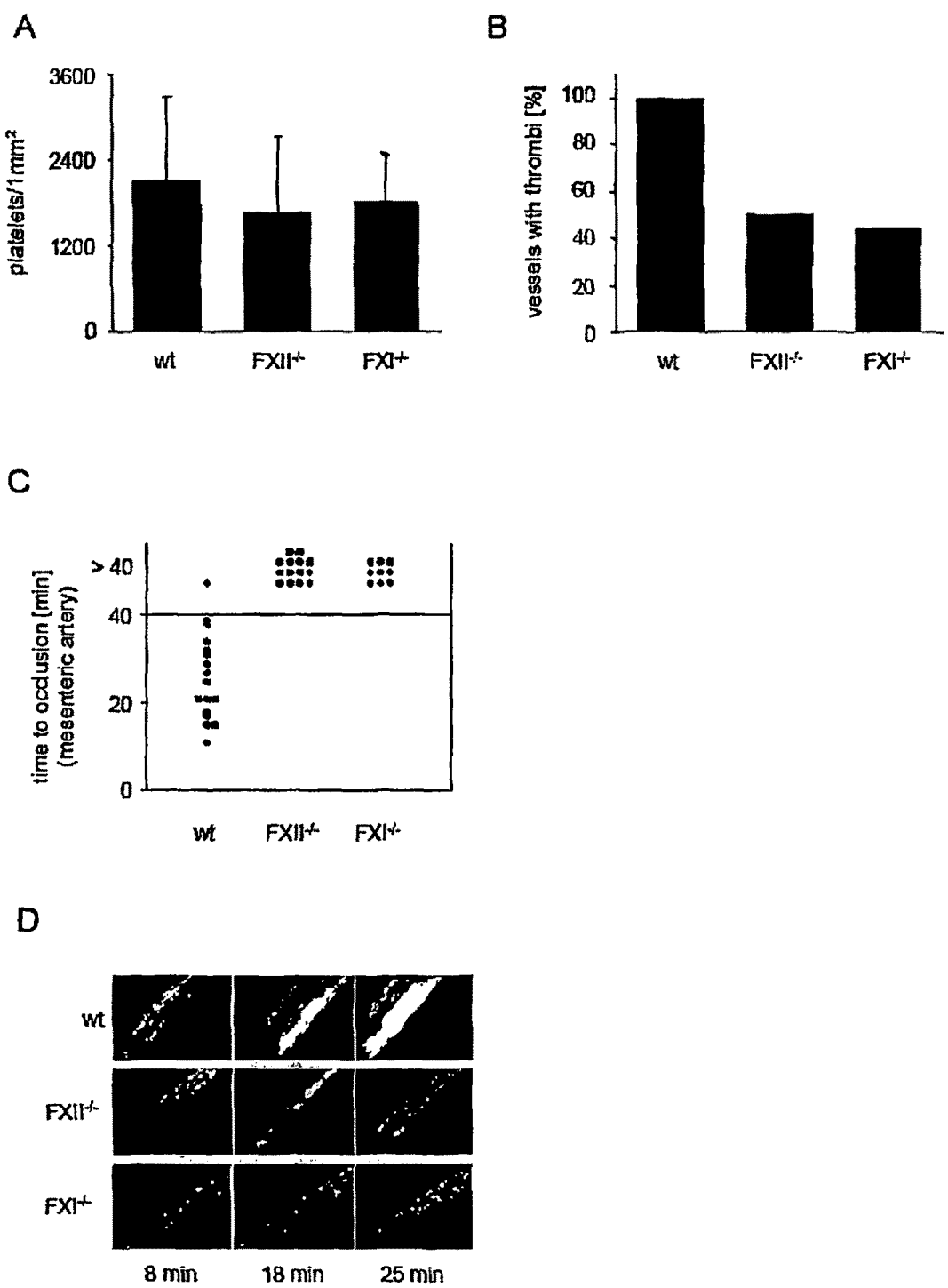

FIG. 3 describes the defective thrombus formation in mice lacking factor XII in vivo. Thrombus formation in vivo was monitored on mesenteric arterioles upon injury induced with 20% FeCl3. (A) Single platelet adhesion is detected 5 min after injury in all mouse strains, 7 to 8 minutes after injury the first thrombi in wt mice were observed, whereas in FXII-/- the first thrombi occurred 14 to 35 minutes after injury and in FXI-/- 5 to 35 minutes after injury. (B) Thrombus formation was observed in 100% of mesenteric arteries in wild type mice, but only in 50% of FXII-/- mice and in 44.4% of FXI-/- mice. (C) Thrombi formed in wt mice occluded the vessel in average 25 minutes after injury whereas thrombi formed in FXII and FXI deficient mice did not lead to occlusion. Each symbol represents one single monitored arteriole. (D) Representative pictures of one experiment.

Figure 4:
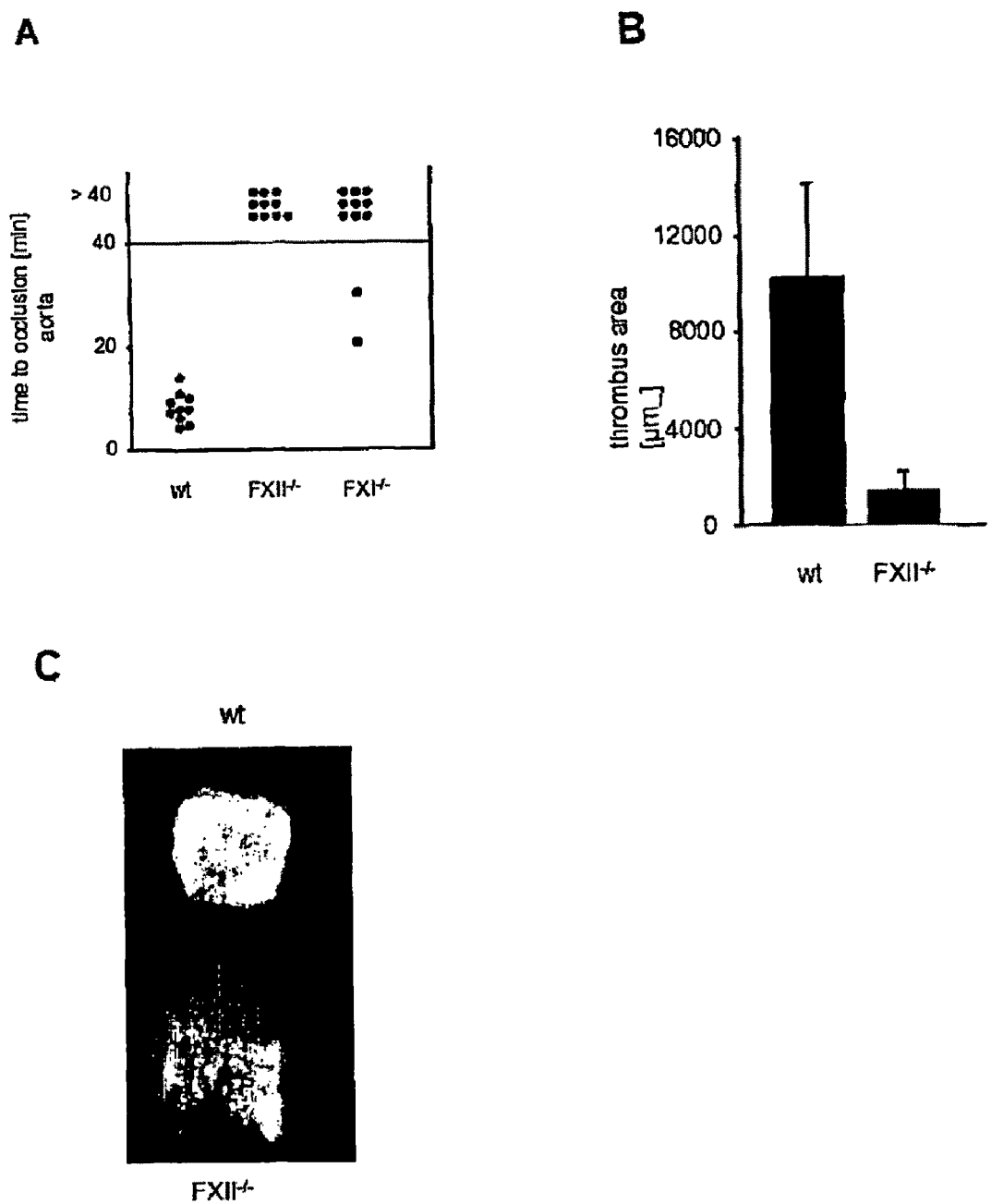

FIG. 4. (A) Wild-type (n=10), FXII-/- (n=10) and FXI-/- (n=11) were analyzed in an arterial occlusion model. Thrombosis was induced in the aorta by one firm compression with a forceps. Blood flow was monitored with an perivascular ultrasonic flow probe until complete occlusion. The experiment was stopped after 40 min. Each symbol represents one individual. (B) Mechanical injury in the carotid artery was induced by a ligation. After removal of the filament thrombus area in wild-type (n=10) and FXII-/- (n=10) was measured in µm2. (C) The photomicrographs show representative images 2 min after injury.

Figure 5:
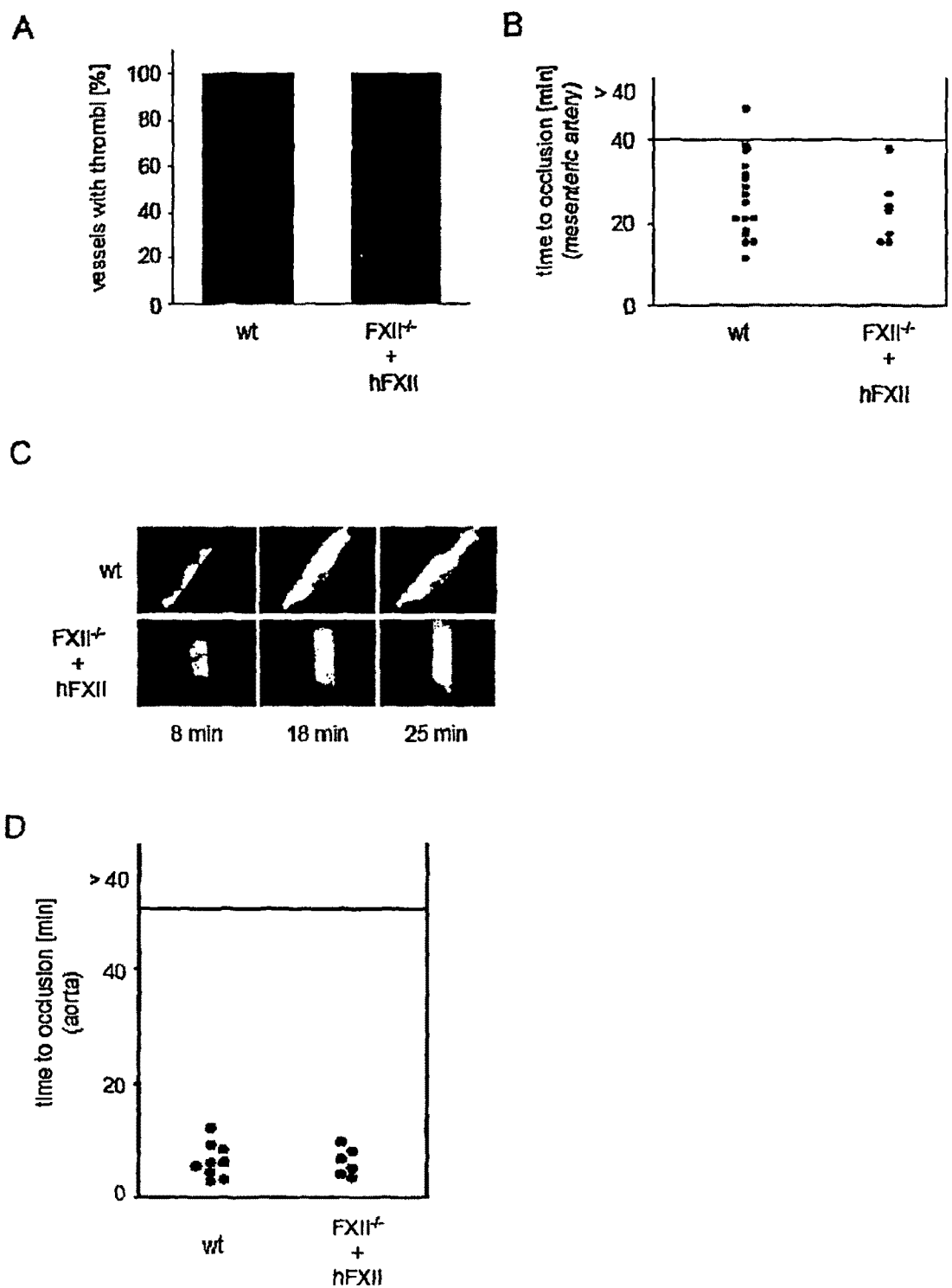

FIG. 5 describes the defect in thrombus formation in FXII deficient animals which is restored by human FXII. (A) Thrombus formation upon $FeCl_3$ induced injury was observed in 100% of mesenteric arteries in wild-type mice as well as in FXII-/- mice injected with human FXII. (B) Formed thrombi occluded the vessel in average 25 minutes after injury in wild-type mice and in 22.7 minutes after injury in FXII-/- mice injected with human FXII. Each symbol represents one individual. (C) Representative pictures are shown. (D) FXII-/- mice received 2 mg/kg hFXII-/- and thrombosis was induced in the aorta by one firm compression with a forceps. Blood flow was monitored with an perivascular ultrasonic flow probe until complete occlusion. The experiment was stopped after 40 min. Each symbol represents one individual.

FIG. 6 describes the anti-FXII antibodies inhibiting thrombus formation in mice in vivo. Wild-type mice received 2 mg/kg anti-FXII antibodies or non-immune IgG i.v. After 15 min, thrombus formation in vivo was monitored on mesenteric arterioles upon injury induced with 20% $FeCl_3$. (A) Single platelet adhesion is detected 5 min after injury in both groups. After 7 to 8 minutes the first thrombi mice in control IgGtreated mice were observed, whereas in anti-FXII-treated mice the first thrombi occurred 12 to 32 minutes after injury. (B) Thrombus formation was observed in 100% of mesenteric arteries in control mice, but only in 60% of anti-FXII-treated mice. (C) Time to complete occlusion is shown. Each symbol represents one individual.

FIG. 7 describes a revised model of arterial thrombus formation. Initially, at sites of vascular lesions thrombin formation is predominantly due to tissue factor (TF) exposure in the subendothelial matrix. TF in complex with FVII initiates the extrinsic pathway of coagulation. At the site of injury the contribution of the FXII driving the intrinsic pathway via FXI for thrombin (FII) generation is minor and negligible for normal hemostasis. Accordingly individuals with FXII-deficiency do not suffer from bleeding. Generated thrombin initiates clot formation by forming fibrin and activating platelets. Propagation of thrombus growth: On surfaces exposed in the growing thrombus the FXII- induced intrinsic pathway critically contributes to thrombin generation. Activated FXII generates additional fibrin through FXI. Accordingly, FXII– as well as FXI– deficiency severely impairs thrombus formation.

In the present invention a potential contribution of the intrinsic pathway of coagulation for pathological thrombus formation in vivo was assessed by intravital microscopy- and flow measurement-based models of arterial thrombosis using mice lacking factor XII. While initial adhesion of platelets at sites of injury is not altered in the mutant animals, the subsequent formation and stabilization of three-dimensional thrombi is severely defective. This defect was seen in different branches of the vasculature and could be completely restored by exogenous human factor XII. These findings establish the factor XII-driven intrinsic coagulation pathway as a major link between primary and secondary hemostasis in a revised model of thrombus formation.

To analyze the function of FXII for clotting in vivo, FXII-deficient mice were generated. FXII–/– mice are healthy, phenotypically indistinguishable from their wild-type littermates, and fertile. Detailed histological and hemostasiological analyses showed no correlates for increased thrombosis or bleeding in FXII–/– mice despite a prolonged aPTT of 68±17 sec and recalcification time of 412±78 sec in retroorbitally collected plasma (wt: 23±4 and 210±31 sec) (Pauer, H. U., et al. (2004). Targeted deletion of murine coagulation factor XII gene—a model for contact phase activation in vivo. Thromb. Haemost. 92, 503-508). Similarly to FXII-deficient humans, FXII–/– mice present with no increased bleeding tendency as indicated by tail bleeding times similar to those found in wild-type animals (369.5±201.7 and 355.9±176.1 sec, respectively, n=12 per group, FIG. 1A). Peripheral blood cell counts of mutant mice did not differ from wild-type controls. Notably, the prothrombin time (PT) of FXII–/– mice was similar to the wild-type (8.9±1.3 vs. 9.1±1.3 sec) indicating that FXII deficiency does not affect fibrin formation by the extrinsic coagulation system (FIG. 1B). To assess potential differences in FXII procoagulant activity between humans and mice, FXII-deficient human (FXII<1%) with murine wild-type plasma or vice versa were reconstituted and the PTT of the mixtures was determined. In either case, clot formation was normalized supporting the notion that FXII function for clotting is comparable in humans and mice.

In humans similarly to FXII deficiency the deficiency of contact system proteins plasma kallikrein (PK) and high molecular weight kininogen (HK) does not result in an increased bleeding risk despite a prolonged aPTT. To confirm that the aPTT prolongation in FXII–/– mice is not due to additional defects of contact phase proteins, we analyzed PK and HK in FXII–/– and wt plasma. The Western blot indicated that HK and PK levels are equivalent in mutant and wild-type mice (FIG. 1C). Functionally, in FXII–/– plasma exposed to collagen or kaolin HK procession and thrombin formation was severely impaired compared to wild-type.

Blood coagulation and platelet activation are complementary and mutually dependent processes. Platelets interact with and contribute to the activation of several coagulation factors and the central coagulation product thrombin is a potent platelet activator. Therefore, next the contribution of platelets and FXII was examined to clot formation in more detail. For this, we induced clotting using either kaolin that classically activates FXII but has no direct effect on platelets or collagen, which activates both FXII and platelets where it interacts with numerous receptors, most importantly α2 β1 integrin and GPVI. In the presence, but not in the absence of platelets, collagen was superior to kaolin for clot formation in wild-type plasma (FIG. 1D). In contrast, in plasma containing activation-defective FcRγ–/– platelets, the relative potency of kaolin and collagen was similar to PFP and a similar effect was seen with PRP from integrin α2–/– mice. Platelet procoagulant activity is also efficiently triggered in coagulating plasma and the fibrin(ogen) receptor αIIbβ3 has been shown to play a crucial role in this process although the underlying mechanisms are not fully understood. In agreement with these reports, the αIIbβ3-function blocking antibody JON/A largely inhibited the platelet-dependent decrease in the clotting time (FIG. 1D). Together, these results demonstrated that platelets in a procoagulant state can promote FXII-induced clot formation.

To test whether collagen-induced FXII activation has functional consequences in vivo, wild-type and FXII–/– mice were subjected to a model of lethal pulmonary thromboembolism induced by the infusion of a mixture of collagen (0.8 mg/kg body weight) and epinephrine (60 µg/kg body weight). All of the control mice (19/19) died within 5 min from widespread pulmonary thrombosis and cardiac arrest which was accompanied by a >95% reduction in circulating platelet counts as soon as 2 min after challenge (FIG. 2 A, B). Under these experimental conditions, 35.7% (5/14) of the FXII–/– mice survived although their peripheral platelet counts were similarly reduced as in the wild-type control, suggesting that the observed protection was not based on a platelet activation defect. This assumption was confirmed by in vitro studies showing that FXII–/– platelets express normal levels of the major surface glycoproteins, including collagen receptors, and that the cells are normally activatable by classical agonists such as thrombin, adenosine diphosphate (ADP), or the GPVI-specific agonist, collagen-related peptide (as measured by activation of integrin αIIbβ3 and P-selectin expression). In agreement with this, FXII–/– platelets exhibited an unaltered aggregation response to collagen, ADP (FIG. 2C), PMA, or thrombin.

In a parallel set of experiments, FcRγ–/– mice were challenged with collagen/epinephrine. These mice were completely protected from lethality and platelet counts were only moderately reduced 2 min after challenge confirming the strict requirement for platelet activation for lethality in this model. These data were further supported by histological analysis of lung sections derived from mice of the different groups. While the large majority of the vessels was obstructed in wild-type mice, this was significantly reduced in FXII–/– mice (survivors and non survivors). In agreement with previous reports, virtually no thrombi were found in lungs from FcRγ–/– mice (FIG. 2D). These results suggested that in vivo collagen triggers both platelet activation and the FXII-dependent intrinsic coagulation pathway which in this model synergize to form occlusive pulmonary thrombi.

Pathological thrombus formation is frequently initiated by fissuring or abrupt disruption of the atherosclerotic plaque in the arterial branch of the vasculature leading to unphysiologically strong platelet activation and procoagulant activity on the surface on the subendothelial layers. To test the role of FXII in these processes, thrombus formation was studied in wild-type and FXII–/– mice, employing different models of arterial injury. In the first model, oxidative injury was induced in mesenteric arterioles (60-100 µm in diameter) and thrombus formation was examined by in vivo fluorescence microscopy. Wild-type and FXII–/– mice received fluorescently labeled platelets (1×108) of the same genotype and injury was induced by topical application of a filter paper saturated with 20% ferric chloride ($FeCl_3$) for 1 min which provokes the formation of free radicals leading to the disruption of the endothelium. Platelet interactions with the injured vessel wall started rapidly and five minutes after injury the number of firmly adherent platelets was similar in both groups of mice (FIG. 3A). However, while in wild-type mice the adherent platelets consistently recruited additional platelets from the circulation, resulting in the formation of aggregates, this process was severely defective in the mutant mice. In 100% of the control vessels (17/17), stable thrombi >20 μm in diameter had formed with 10 min after injury which continuously grew over time and finally lead to complete occlusion in 94.1% (16/17) of the vessels within the observation period of 40 min (mean occlusion time: 25.6±8.9 min) (FIG. 3). In sharp contrast, in mutant mice the formation of microaggregates or thrombi occurred was completely absent in 50% (7/14) of the vessels. In the remaining 50% (7/14) of the vessels, thrombi were formed which were, however, consistently unstable and rapidly detached from the vessel wall. In none of the vessels, a thrombus >20 μm in diameter remained attached at the site of injury for more than 1 min. Consequently, no vessel occluded in FXII−/− mice within the observation period (40 min). This unexpected result demonstrated that FXII is required for the generation and stabilization of platelet-rich thrombi in $FeCl_3$-injured arterioles and suggested that FXII-induced the coagulation pathway essentially contributes to the observed thrombotic response. This assumption was confirmed when mice deficient in FXI were analysed in the same model. Since FXI is the principal substrate of FXII in the "intrinsic" cascade, a similar defect in thrombus formation would have to be expected in those mice. Indeed, very similar to FXII−/− mice, virtually normal platelet adhesion at the site of injury was detectable during the first three minutes after injury, whereas the form ation of thrombi was completely inhibited in 55.6% (5/9) of the vessels. In the remaining vessels, the formed microaggregates and thrombi were unstable and continuously embolized (FIG. 3). As a result, none of the vessels occluded within the observation period (40 min). This data shows that FXI-deficient mice are protected in a model of $FeCl_3$-induced occlusion of the carotid artery.

$FeCl_3$-induced arterial thrombus formation is known to depend on platelets and thrombin generation but it is unclear how well this type of injury resembles the thrombogenic milieu produced in diseased vessels, e.g. upon rupture of the atherosclerotic plaque. Therefore, to exclude the possibility that the massive $FeCl_3$-induced oxidative damage produces unphysiological conditions which may artificially favor FXII-dependent contact phase activation, the function of FXII was assessed in a second well-established arterial thrombosis model where injury is induced mechanically in the aorta and blood flow is monitored with an ultrasonic flow probe. After a transient increase directly after injury, blood flow progressively decreased for several minutes in all mice tested. In all tested wild-type mice (10/10), this decrease resulted in complete and irreversible occlusion of the vessel within 1.6 to 11.1 min after injury (mean occlusion time 5.3±3.0 min, FIG. 4A). A different picture was found in FXII−/− mice where stable thrombus formation was severely defective. While in all animals a progressive reduction in blood flow was observed during the first minutes after injury, occlusion occurred only in 4 of 10 mice. Moreover, the occlusive thrombi in those mice were in all cases unstable and rapidly embolized so that blood flow was re-established between 10 s and 115 s after occlusion. None of the re-opened vessels occluded a second time. Consequently, all FXII−/− mice displayed essentially normal flow rates through the injured vessel at the end of the observation period (40 min). Very similar results were obtained with FXI−/− mice, where 9 of 11 were unable to establish an occlusive thrombus within the observation period (30 min) (FIG. 5A).

The severe defect in arterial thrombus formation in FXII−/− mice was confirmed in a third independent model where platelet recruitment in the injured carotid artery was studied by in vivo fluorescence microscopy. Platelets were purified from donor mice, fluorescently labeled and injected into recipient mice of the same genotype. Vascular injury was induced by vigorous ligation of the carotid artery which consistently causes disruption of the endothelial layer and frequently breaching of the internal elastic lamina followed by rapid collagen-triggered platelet adhesion and thrombus formation at the site of injury (Gruner et al., Blood 102:12/8/ 2005 2003). While wild-type animals rapidly formed large stable thrombi (thrombus area: 102.821±39.344 μm2; t=5 min), which did not embolize, only small and mediumsized aggregates formed in the mutant mice, which were frequently detached from the site of injury (FIG. 4B, C). Consequently, the thrombus area was dramatically reduced in the mutant mice (8.120±13.900 μm2; t=5 min) although primary platelet adhesion on the vessel wall appeared not to be defective.

To test whether the severe defect in thrombus formation in FXII−/− mice results from the lack of plasma FXII or platelet FXII, or possibly from secondary, unidentified effects of FXII deficiency such as alterations in the vasculature, arterial thrombus formation was studied in FXII−/− mice following administration human of FXII (2 μg/g body weight). This treatment normalized the PTT (27±6 sec) and fully restored arterial thrombus formation. In 100% of the FeCl3-injured mesenterial arterioles, thrombi >20 μm had formed within 10 min after injury and all of the vessels completely occluded within the observation period (FIG. 5A-C). There was even a tendency towards faster occlusion detectable in the reconstituted FXII−/− mice as compared to untreated wild-type control mice (mean occlusion time: 22.7±8.2 min vs. 25.6±8.9 min). A similar result was obtained when injury was induced mechanically in the aorta. In all tested vessels, complete and irreversible occlusion occurred within 10 min after injury (FIG. 5D), confirming that the lack of plasma FXII accounts for the thrombotic defect observed in FXII−/− mice.

The above-described studies demonstrated that FXII is crucial for arterial thrombus formation and may, therefore, serve as an antithrombotic target.

To assess this directly, mice were treated with 2 mg/kg body weight polyclonal rabbit anti-mouse FXII antibodies or non-immune rabbit antibodies and assessed platelet recruitment and thrombus formation in mesenterial arteries following $FeCl_3$-induced injury. As shown in FIG. 6A, platelet adhesion at sites of injury was comparable in both groups of mice. However, while in 100% of the control vessels, thrombi >20 μm had formed within 10 min after injury and all of the vessels completely occluded within the observation period (FIG. 6B, C), thrombi >20 μm were only observed in 67% of the vessels and occlusion occurred only in 50% of the vessels of the animals treated with anti-FXII antibody.

Alternatively, to test the impact of small molecule FXII inhibitors, wildtype mice were infused with the FXII inhibitor corn trypsin inhibitor (CTI, 50 μg/g body weight) 5 min prior to $FeCl_3$-induced injury in the carotic artery (Wang et al. (2005) J. Thromb. Heamost. 3: 695-702). Inhibitor treatment prolonged the aPTT (62±11 sec, n=4) but did not affect bleeding during the surgical procedure. In none of the animals tested (0/4) vessel occluding thrombi developed within 30 min following application of $FeCl_3$.

These results demonstrated that anti-FXII therapeutics like anti-FXII antibodies or small molecule FXII inhibitors provide significant protection against arterial thrombus formation.

Although contact activation of FXII has been recognized as the starting point of the intrinsic blood coagulation cascade for more than 50 years this pathway was considered to be irrelevant for blood clotting. In the present invention, three different in vivo models were used to analyze platelet recruitment and thrombus formation at sites of arterial injury in FXII-deficient mice by in situ video microscopy and ultrasonic flow measurements and showed a severe inability to form stable three-dimensional thrombi. This defect was based on the lack of FXII in plasma, but not other compartments, as it was completely reversed by intravenous injection of exogenous human FXII (FIG. 6) thereby also excluding that secondary effects of FXII deficiency contribute to the observed phenotype.

These results are unexpected as FXII has been regarded as an anti-thrombotic rather than a prothrombotic enzyme based on a few reports showing an association of FXII-deficiency with an increased incidence of venous thrombosis (Kuhli, C., Scharrer, I., Koch, F., Ohrloff, C., and Hattenbach, L. O. (2004). Factor XII deficiency: a thrombophilic risk factor for retinal vein occlusion. Am. J. Opthalmol. 137, 459-464; Halbmayer, W. M., Mannhalter, C., Feichtinger, C., Rubi, K., and Fischer, M. (1993). [Factor XII (Hageman factor) deficiency: a risk factor for development of thromboembolism. Incidence of factor XII deficiency in patients after recurrent venous or arterial thromboembolism and myocardial infarction]. Wien. Med. Wochenschr. 143, 43-50).

FXII-deficient mice display normal bleeding times (FIG. 1A) and do not show signs of spontaneous or increased post-traumatic (intraoperative) bleeding confirming that FXII is dispensable for normal hemostasis. At the first sight, these results seem to contradict with a central dogma of hemostasis that only those factors whose deficiency is associated with bleeding or thrombosis are relevant to blood clotting. On a closer look, however, the data do not challenge this theorem but rather raise the interesting possibility that hemostasis and arterial thrombosis may occur through different mechanism.

Although the above discussed mechanisms of sustained thrombin generation may be sufficient to generate a hemostatic plug, the data show that the formation of stable arterial thrombi requires the additional activation of the intrinsic coagulation pathway, at least in mice. There is no evidence for the possibility that speciesspecific differences exist in the function of FXII or a substrate of the enzyme. All coagulation parameters and the hemostatic phenotype of the mutant mice are in line with human FXII-deficiency and all alterations observed in animals were normalized by reconstitution with human FXII (FIG. 5). Furthermore, it is excluded that the thrombotic defect is restricted to a particular experimental model as it was found in different arterial branches of the vasculature and independent of the type of injury. It may be difficult to determine what type of damage best reflects the vascular lesion produced by rupture of an atherosclerotic plaque, which is considered the major trigger of acute cardiovascular syndromes. Atherosclerotic lesions are rich in thrombogenic constituents, most importantly TF and fibrillar collagens. In the process of atherogenesis, enhanced collagen synthesis by intimal smooth muscle cells and fibroblasts has been shown to significantly contribute luminal narrowing. Plaque rupture or fissuring results in exposure of collagen fibrils to the flowing blood which triggers platelet adhesion and aggregation. In addition, they induce FXII activation as shown here for fibrillar collagen type I, which is the major collagen type found in the vessel wall. But the collagens are likely not the only (patho)physiological activator of FXII at sites of injury. Other candidates could be substances liberated from disintegrating cells or exposed in the ECM including HSP90 or soluble and insoluble polyanions, e.g. nucleosomes or glycosaminoglycans.

Among these FXII activators, collagens are by far most thrombogenic because they also potently activate platelets. At sites of injury, platelets tether to the ECM by the reversible interaction of platelet GPIb-V-IX with collagen-bound vWf which reduces the velocity of the cells and thereby allows binding of other receptors. Among these, the collagen receptor GPVI is of central importance as it activates integrins $\alpha2\beta1$ and $\alpha IIb\beta3$ which then mediate stable adhesion and contribute to cellular activation. In addition, platelet activation through the GPVI/FcR$\gamma$-chain complex induces a procoagulant state of the cells which is characterized by the exposure of phosphatidylserine (PS) and the production of (PS exposing) membrane blebs and microvesicdes. Integrin $\alpha2\beta1$ facilitates this process directly by "outside-in" signals and indirectly by reinforcing GPVI-collagen interactions. It is established that PScontaining membranes strongly accelerate two central reactions of the coagulation process, the tenase and prothrombinase reactions. The present invention shows that procoagulant platelets facilitate FXII-dependent clotting in vitro by a mechanism involving both the GPVI/FcR$\gamma$-chain complex as well as $\alpha2\beta1$ (FIG. 2). This could at least partly explain why $\alpha2\beta1$-deficient mice, despite unaltered platelet adhesion at sites of arterial injury, show partial defects in the formation of occlusive thrombi. Besides collagens, coagulating plasma potently stimulates platelet procoagulant activity by an integrin $\alpha IIb\beta3$-dependent mechanism. In the present experiments, $\alpha IIb\beta3$ blockade almost completely inhibited platelet participation in FXII-dependent clotting, indicating that the well-known anticoagulant activity of $\alpha IIb\beta3$ antagonists may partly be based on the inhibition of the FXII-driven intrinsic coagulation pathway. Together, the present invention indicates that the FXII-driven contact system and platelet activation may be mutually dependent processes that cooperate in pathological thrombus formation.

Based on the experimental results, a model of pathological thrombus formation depicted schematically in FIG. 7 was proposed. At sites of vascular injury, the first layer of platelets comes in contact with collagens in an environment that is additionally enriched in TF and fibrin. It is therefore not surprising that platelet adhesion to the damaged vessel wall is not impaired in FXII–/– mice and it is very likely that these cells were fully activated and in a procoagulant state. In a growing thrombus, however, collagens are absent and TF concentrations provided by microvesicles may be lower as compared to the vessel wall and reduced in their activity by TFPI released in large amounts from activated platelets. Under these conditions, additional mechanisms are required to maintain spatio-temporal thrombin generation to activate newly recruited platelets and, via the formation of fibrin provoke their coagulant activity. The severe inability of FXII–/– mice to establish stable thrombi unambiguously demonstrates that the FXII-driven intrinsic coagulation pathway is an essential player in this process. Together with the observation that low TF-mice also display impaired arterial thrombosis, these results suggest that both extrinsic and intrinsic pathway must be operative and synergize to promote the formation of a three-dimensional and eventually occluding thrombus. In contrast, the lack of bleeding in FXII–/– mice indicates that thrombus growth in the third dimension may not be necessary to seal a hole in the vessel wall. This could explain why the extrinsic pathway, which produces the first thin layer of fibrin and activated platelets, is sufficient to mediate normal hemostasis. Our results raise the interesting possibility the formation of a three-dimensional thrombus serves functions other than hemostasis. These could include the arrest of blood flow in certain areas of tissue trauma in order to prevent the distribution of invading pathogens or toxins with the blood stream.

Experimental Procedures

Animals

All experiments and care were approved by the local Animal Care & Use Committee. Classical mouse mutants lacking factor XI (FXI−/−), factor XII (FXII−/−), α2 integrin (α2−/−) were produced as described (Gailani, D., Lasky, N. M., and Broze, G. J., Jr. (1997). A murine model of factor XI deficiency. Blood Coagul. Fibrinolysis 8, 134-144; Pauer, H. U., Renne, T., Hemmerlein, B., Legler, T., Fritzlar, S., Adham, I., Muller-Esterl, W., Emons, G., Sancken, U., Engel, W., and Burfeind, P. (2004). Targeted deletion of murine coagulation factor XII gene—a model for contact phase activation in vivo. Thromb. Haemost. 92, 503-508; Holtkotter, O., Nieswandt, B., Smyth, N., Muller, W., Hafner, M., Schulte, V., Krieg, T., and Eckes, B. (2002). Integrin alpha 2-deficient mice develop normally, are fertile, but display partially defective platelet interaction with collagen. J Biol Chem JID-2985121R 277, 10789-10794). As a control C57B/6J mice (FXI−/−) or Sv129 (FXII−/−) were used. Mice deficient in the FcRγ-chain (Takai, T., Li, M., Sylvestre, D., Clynes, R., and Ravetch, J. V. (1994). FcR gamma chain deletion results in pleiotrophic effector cell defects. Cell 76, 519-529) were from (Taconics, Germantown).

Generation of Anti-FXII Antibodies

Total cellular RNA was isolated from a liver of a 129sv wt mouse and the FXIIcDNA synthesis was performed with the "one-step RT-PCR Kit" from Qiagen according to the manufacturers instructions. The factor FXII heavy chain (positions 61-1062, corresponding to residues 21-354) was amplified using 25 pmol each of the 5- and 3-primers (ttggatccccaccatg-gaaagactccaag and ttgaattcgcgcatgaacgaggaca g) introducing a BamH I and EcoR I restriction site, respectively with the following protocol: 30 s at 95° C., 60 s at 58° C., and 1 min at 72° C. for 30 cycles on a thermal cycler (Biometra, Göttingen, Germany). The PCR product was cloned into the BamH I and EcoR I site of the pGEX-2T expression vector (Pharmacia). Following sequencing protein was expressed in *E. coli* strain BL21. Exponentially growing bacteria were stimulated with 0.5 mM isopropyl-β-D-thiogalactopyranoside for 1 h, harvested, resuspended in 10 mM Tris-HCl, pH 7.4, containing 1 mM EDTA, 200 mM NaCl, 10 μg/ml benzamidine hydrochloride, 10 μg/ml phenylmethylsulfonyl fluoride and sonicated for 3 min in pulses of 15 s each. After centrifugation at 15,000×g for 20 min at 4° C., the supernatant was removed and transferred to a GST-sepharose column (Pharmacia) for purification. Eluted protein was >95% pure as deduced from Coomassie stained SDS-PAGE. Polyclonal antibodies against GST-heavy chain FXII were raised in rabbits following standard procedures. Antibodies were selected from the hyperimmunserum using columns with FXIIheavy chain fused to the maltose binding protein (MBP). These fusion proteins were expressed and purified using the pMAL-c2 expression system and amylose resin columns similarly as described for the GST-fusion construct.

Platelet Preparation

Mice were bled under ether anesthesia from the retroorbital plexus. Blood was collected in a tube containing 20 U/mL heparin, and platelet rich plasma (prp) was obtained by centrifugation at 300 g for 10 min at room temperature (RT). For washed platelets, prp was centrifuged at 1000 g for 8 min and the pellet was resuspended twice in modified Tyrodes-Hepes buffer (134 mM NaCl, 0.34 mM Na2HPO4, 2.9 mM KCl, 12 mM NaHCO3, 20 mM Hepes, 5 mM glucose, 0.35% bovine serum albumin, pH 6.6) in the presence of prostacyclin (0.1 μg/ml) and apyrase (0.02 U/mL). Platelets were then resuspended in the same buffer (pH 7.0, 0.02 U/mL of apyrase) and incubated at 37° C. for at least 30 min before analysis.

Flow Cytometry

Heparinized whole blood was diluted 1:20 with modified Tyrode-HEPES buffer (134 mM NaCl, 0.34 mM Na2HPO4, 2.9 mM KCl, 12 mM NaHCO3, 20 mM HEPES [N-2-hydroxyethylpiperazine-N'-2-ethanesulfonic acid], pH 7.0) containing 5 mM glucose, 0.35% bovine serum albumin (BSA), and 1 mM CaCl2. The samples were incubated with fluorophore-labeled antibodies for 15 minutes at room temperature and directly analyzed on a FACScalibur (Becton Dickinson, Heidelberg, Germany) (Nieswandt, B., Schulte, V., and Bergmeier, W. (2004). Flow-cytometric analysis of mouse platelet function. Methods Mol. Biol. 272, 255-268).

Aggregometry

To determine platelet aggregation, light transmission was measured using prp (200 μL with 0.5×106 platelets/μL). Transmission was recorded in a Fibrintimer 4 channel aggregometer (APACT Laborgeräte und Analysensysteme, Hamburg, Germany) over 10 min and was expressed as arbitrary units with 100% transmission adjusted with plasma. Platelet aggregation was induced by addition of collagen (10 μg/mL) and ADP (5 μM).

Bleeding Time Experiments

Mice were anesthetized by intraperitoneal injection of tribromoethanol (Aldrich) (0.15 ml/10 g of body weight) and 3 mm segment of the tail tip was cut off with a scalpel. Tail bleeding was monitored by gently absorbing the bead of blood with a filter paper without contacting the wound site. When no blood was observed on the paper after 15 second intervals, bleeding was determined to have ceased. When necessary, bleeding was stopped manually after 20 minutes. Where indicated, mice were treated with 100 μg/mouse of hFXII.

Preparation of Platelets for Intravital Microscopy

Mouse blood (1 vol) was collected into 0.5 vol of Hepes buffer containing 20 U/mL heparin. The blood was centrifuged at 250 g for 10 minutes and platelet-rich plasma was gently transferred to a fresh tube. Platelets were labelled with 5-carboxyfluorescein diacetate succinimidyl ester (DCF) and adjusted to a final concentration of 200×106 platelets/250 μl (Massberg, S., Sausbier, M., Klatt, P., Bauer, M., Pfeifer, A., Siess, W., Fassler, R., Ruth, P., Krombach, F., and Hofmann, F. (1999). Increased adhesion and aggregation of platelets lacking cyclic guanosine 3',5'-monophosphate kinase I. J Exp Med 189, 1255 1263).

In Vivo Thrombosis Model with FeCl3-Induced Injury.

Male and female mice in the age of 4-5 weeks were anesthetized by intraperitoneal injection of 2,2,2-tribromoethanol and 2-methyl-2-butanol (Sigma) (0.15 ml/10 g of body weight from 2.5% solution). Fluorescently labeled platelets were injected intravenously. Mesentery was exteriorized gently through a midline abdominal incision. Arterioles (35-50 μm diameter) were visualized with a Zeiss Axiovert 200 inverted microscope (×10) equipped with a 100-W HBO fluorescent lamp source and a CCD camera (CV-M300) connected to an S-VHS video recorder (AG-7355, Panasonic, Matsushita Electric, Japan). After topical application of FeCl3 (20%) which induced vessel injury and denudation of the endothelium, were arterioles monitored for 40 min or until complete occlusion occurred (blood flow stopped for >1 min). Firm platelet adhesion is determined as number of fluorescently labeled platelets that deposited on the vessel wall until 5 minutes after injury, thrombus is characterized as a platelet aggregate in a diameter larger than 20 µm, occlusion time of vessel is characterized as time required for blood to stop flowing for at least one minute. In all experiments maximum of two arterioles were chosen from each mouse based on quality of exposure. A total of 17 wt, 14 FXII−/− and 9 FXI−/− arterioles were studied.

Intravital Microscopy—Carotid Artery

Intravital microscopy of the injured carotid artery was performed essentially as described (Massberg, S., Gawaz, M., Gruner, S., Schulte, V., Konrad, I., Zohinhofer, D., Heinzmann, U., and Nieswandt, B. (2003). A crucial role of glycoprotein VI for platelet recruitment to the injured arterial wall in vivo. J Exp Med JID-2985109R 197, 41-49). Briefly, mice were anesthetized by intraperitoneal injection of ketamine/xylazine (ketamine 100 mg/kg, Parke-Davis, Karlsruhe, Germany; xylazine 5 mg/kg, Bayer AG, Leverkusen, Germany). Polyethylene catheters (Portex, Hythe, England) were implanted into the right jugular vein and fluorescent platelets (200×106/250 µl) were infused intravenously. Carotid injury for endothelial denudation was induced by vigorous ligation. Prior to and following vascular injury, the fluorescent platelets were visualized in situ by in vivo video microscopy of the right common carotid artery using a Zeiss Axiotech microscope (20× water immersion objective, W 20×/0.5, Zeiss, Göttingen, Germany) with a 100 W HBO mercury lamp for epi-illumination. Platelet adhesion and thrombus formation was recorded for 5 min after the induction of injury and the video-taped images were evaluated using a computer-assisted image analysis program (Visitron, Munich, Germany).

Pulmonary Thromboembolism

Mice were anesthetized by intraperitoneal injection of 2,2, 2-tribromoethanol and 2-methyl-2-butanol (Aldrich) (0.15 ml/10 g of body weight from 2.5% solution). Anesthetized mice received a mixture of collagen (0.8 mg/kg) and epinephrine (60 µg/kg) injected into the jugular vein. The incisions of surviving mice were stitched, and they were allowed to recover. Necroscopy and histological studies were performed on lungs fixed in 4% formaldehyde and paraffin sections were stained with hematoxylin/eosin.

Platelet Count

Platelet count was determined by flow cytometry on a FACScalibur (Becton Dickinson, Heidelberg, Germany). Results are expressed as mean±S.D or as percent of control (wt, n=19; FXII−/−, n=14 and FcRγ−/−, n=5).

Occlusion Time

The abdominal cavity of anesthetized mice was longitudinally opened and the abdominal aorta was prepared. An ultrasonic flow probe was placed around the aorta and thrombosis was induced by one firm compression with a forceps. Blood flow was monitored until complete occlusion occurred. The experiment was stopped manually after 45 minutes. Where indicated, human Factor XII was substituted intravenously directly before the experiment.

Histopathologic Analyses

Mice were sacrificed, lungs rapidly removed and fixed at 4 C for 24 hr in buffered 4% formalin (pH 7.4; Kebo). Tissues were dehydrated and imbedded in paraffin (Histolab Products AB), cut into 4 µm sections, and mounted. After removal of the paraffin, tissues were stained with Mayers hematoxylin (Histolab Products AB) and eosin (Surgipath Medical Industries, Inc.).

SDS-Polyacrylamide Gel Electrophoresis, Western Blotting, and Immunoprinting

Plasma (0.3 µl/lane) was separated by 12.5% (w/v) polyacrylamide gel electrophoresis in the presence of 1% (w/v) SDS (Laemmli, 1970). Proteins were transferred onto nitrocellulose membranes for 30 min at 100 mA. The membranes were blocked with PBS containing 4% (w/v) dry milk powder and 0.05% (w/v) Tween-20, pH 7.4. Membranes were probed with 0.5 µg/ml of the monoclonal antibody against MBK3 (Haaseman J. Immunology 4-1991). Bound antibodies were detected using peroxidase-conjugated secondary antibodies against mouse IgG (dilution 1:5000) followed by a chemiluminescence detection method.

Coagulation Assays.

For the determination of the recalcification clotting time, 100 µl citrate anticoagulated mouse plasma (0.38% sodium citrate), was incubated with 100 µl each of Horm type collagen (Nycomed, Munchen, Germany), ellagic acid, chondroitin sulfate (both from Sigma), kaolin or buffer (final concentrations 30 µg/ml) for 120 sec at 37° C. in a KC10 "Kugelkoagulometer" (Amelung, Lemgo, Germany). To test the effect of platelets activation on FXII-dependent clotting washed platelets were resuspended in Tyrode buffer including 4 mM Ca2+ and 5 µM Ca2+-ionophor A23187 (Sigma) for 10 min prior to addition to platelet free plasma. Clot formation was initiated by recalcification with 100 µl 25 mM CaCl2-solution, and the time until clotting occurred was recorded using the coagulation timer KC4 (Amelung).

Coagulation Analysis

Global and single coagulation parameters were determined with an automated blood coagulation system (BCS, Dade Behring) with Dade Behring reagents according to the protocols for human samples detailed by the manufacturer. Principles of BCS assay protocols are available from Dade Behring package inserts, which can be found on Dade Behring's web site (http://www.dadebehring.com). D-dimers were measured with the ELISA from Asserachrom (Roche). Peripheral blood counts were determined on the Sysmex XE 2100 according to standard protocols.

Thrombin Measurements

Thrombin generation was measured according to the method of Aronson et al. (Circulation, 1992), with slight modifications. Platelet-rich or platelet free plasma aliquots (0.5 ml) were placed into round-bottomed polypropylene tubes that were coated with Horms type collagen (100 µg/ml, 24 h, 4° C.), and 20 µl of 1 M Ca2+ was added to initiate clotting. Samples (10 µl) were added to the wells of a microtiter plate containing 90 µl of 3.8% sodium citrate at 2.5-10 min intervals for 60 min. Color was developed for 2 min by the addition of 50 1 of 2 mmol/liter S-2238 a thrombin-specific substrate; Chromogenix, Mölndal, Sweden) in 1 mol/liter Tris (pH 8.1). The absorbance of the released color product was measured spectrophotometrically at a wavelength of 405 nm using a Vmax microtiter plate reader (Easy Reader, EAR 340AT, SLT Lab Instruments GmbH, Vienna, Austria). Measurements were obtained in triplicate at each time point.

Statistical Evaluation

Statistical analysis was performed using the unpaired Student's t test.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A method of treating a patient at risk for the formation and/or the stabilization of thrombi comprising administering to said patient at least one inhibitor of Factor XII or activated Factor XII (collectively FXII), wherein the at least one inhibitor is at least one anti-FXII antibody, and wherein the patient has, has had, or is at risk for: venous thrombosis, arterial thrombosis, stroke, myocardial infarction, or use of a prosthetic device.

2. The method of claim 1, wherein the prosthetic device is a haemodialyser, cardiopulmonary by-pass circuit, vascular stent, or in-dwelling catheter.

3. The method of claim 1, wherein the patient has, has had, or is at risk for venous thrombosis.

4. The method of claim 1, wherein the patient has, has had, or is at risk for arterial thrombosis.

5. The method of claim 1, wherein the patient has, has had, or is at risk for stroke.

6. The method of claim 1, wherein the patient has, has had, or is at risk for myocardial infarction.

7. A method of treating a patient at risk for the formation and/or the stabilization of thrombi comprising administering to said patient at least one inhibitor of Factor XII or activated Factor XII (collectively FXII), wherein the at least one inhibitor is at least one anti-FXII antibody which inhibits the activation of FXII, wherein said anti-FXII antibody reduces or prevents the formation and/or the stabilization of thrombi, and wherein the patient has, has had, or is at risk for: venous thrombosis, arterial thrombosis, stroke, myocardial infarction, or use of a prosthetic device.

8. The method of claim 7, wherein the prosthetic device is a haemodialyser, cardiopulmonary by-pass circuit, vascular stent, or in-dwelling catheter.

9. The method of claim 7, wherein the patient has, has had, or is at risk for venous thrombosis.

10. The method of claim 7, wherein the patient has, has had, or is at risk for arterial thrombosis.

11. The method of claim 7, wherein the patient has, has had, or is at risk for stroke.

12. The method of claim 7, wherein the patient has, has had, or is at risk for myocardial infarction.

* * * * *